US009545248B2

(12) United States Patent
Taylor et al.

(10) Patent No.: US 9,545,248 B2
(45) Date of Patent: *Jan. 17, 2017

(54) BLUNT TIP OBTURATOR (71) Applicant: Applied Medical Resources Corporation, Rancho Santa Margarita, CA (US)

(72) Inventors: Scott V. Taylor, Rancho Santa Margarita, CA (US); Matthew A. Wixey, San Jose, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/082,558

(22) Filed: Nov. 18, 2013

(65) Prior Publication Data

US 2014/0121695 A1 May 1, 2014
US 2016/0345948 A9 Dec. 1, 2016

Related U.S. Application Data (63) Continuation of application No. 13/411,244, filed on Mar. 2, 2012, now Pat. No. 8,608,768, which is a
(Continued)

(51) Int. Cl.
*A61B 17/02* (2006.01)
*A61B 17/34* (2006.01)
*A61B 17/32* (2006.01)

(52) U.S. Cl.
CPC ........... *A61B 17/02* (2013.01); *A61B 17/3417* (2013.01); *A61B 2017/320044* (2013.01); *A61B 2017/346* (2013.01); *A61B 2017/3456* (2013.01)

(58) Field of Classification Search
CPC ................ A61B 17/02; A61B 17/3417; A61B 2017/3456–2017/346; A61B 17/320016; A61B 2017/320044
(Continued)

(56) References Cited

U.S. PATENT DOCUMENTS 184,573 A 11/1876 Becker
207,932 A 9/1878 Alvord
(Continued)

FOREIGN PATENT DOCUMENTS

BE 1 006 811 12/1994
CA 2 170 841 9/1997
(Continued)

OTHER PUBLICATIONS

U.S. Appl. No. 10/745,262, filed Dec. 23, 2003; Title: "Catheter With Conduit Traversing Tip" (abandoned).
(Continued)

*Primary Examiner* — Kathleen Holwerda
(74) *Attorney, Agent, or Firm* — Rimas T. Lukas (57) ABSTRACT

A surgical obturator comprising an elongate shaft extending along an axis between a proximal end and a distal end includes a bladeless tip disposed at the distal end of the shaft. The tip has a blunt point and a pair of shorter side surfaces separated by a relatively longer pair of opposing surfaces to form in radial cross-section a geometric shape that has a longer length and relatively narrower width. The side surfaces and opposing surfaces terminate in end surfaces located proximally from the blunt point. The end surfaces extend radially outwardly from opposite locations of the outer surface. A conical surface facilitates initial insertion of the obturator and the geometric shape facilitates separation of consecutive layers of muscle tissue having fibers oriented
(Continued)

in different directions and provides proper alignment of the tip between the layers of muscle.

15 Claims, 6 Drawing Sheets

Related U.S. Application Data continuation of application No. 12/836,023, filed on Jul. 14, 2010, now Pat. No. 8,152,828, which is a continuation of application No. 10/514,313, filed as application No. PCT/US03/14924 on May 13, 2003, now Pat. No. 7,758,603.

(60) Provisional application No. 60/381,469, filed on May 16, 2002.

(58) Field of Classification Search
USPC .................................................. 606/184, 190
See application file for complete search history.

(56) References Cited

U.S. PATENT DOCUMENTS

| | | |
|---|---|---|
| 224,513 A | 2/1880 | Burdon |
| 396,754 A | 1/1889 | Mayfield |
| 764,322 A | 7/1904 | Wiegand |
| 1,147,408 A | 7/1915 | Kelis |
| 1,672,258 A | 6/1928 | Hippenmeyer |
| 1,727,495 A | 9/1929 | Wappler |
| 1,845,727 A | 2/1932 | Slaughter |
| 2,024,069 A | 12/1935 | Sharp |
| 2,102,274 A | 12/1937 | Larimore |
| 2,189,343 A | 2/1940 | Fritz |
| 2,301,338 A | 11/1942 | Smith |
| 2,434,594 A | 1/1948 | Schultz |
| 2,441,143 A | 5/1948 | Gracey |
| 2,646,701 A | 7/1953 | Lietin |
| 2,699,770 A | 1/1955 | Fourestier et al. |
| 2,764,148 A | 9/1956 | Sheldon |
| 2,764,149 A | 9/1956 | Sheldon |
| 2,769,355 A | 11/1956 | Henry |
| 2,877,368 A | 3/1959 | Sheldon |
| 2,932,294 A | 4/1960 | Fourestier et al. |
| 3,005,468 A | 10/1961 | Erwin et al. |
| 3,021,834 A | 2/1962 | Sheldon |
| 3,033,226 A | 5/1962 | Allen |
| 3,042,022 A | 7/1962 | Sheldon |
| 3,224,320 A | 12/1965 | Knudsen |
| 3,277,922 A | 10/1966 | Eisel |
| 3,279,460 A | 10/1966 | Sheldon |
| 3,357,433 A | 12/1967 | Fourestier et al. |
| 3,385,553 A | 5/1968 | Braun |
| 3,417,745 A | 12/1968 | Sheldon |
| 3,437,747 A | 4/1969 | Sheldon |
| 3,459,189 A | 8/1969 | Alley et al. |
| 3,556,085 A | 1/1971 | Takahashi |
| 3,613,684 A | 10/1971 | Sheridan |
| 3,653,338 A | 4/1972 | Sauey |
| 3,791,379 A | 2/1974 | Storz |
| 3,817,251 A | 6/1974 | Hasson |
| 3,821,956 A | 7/1974 | Gordhamer |
| 3,870,036 A | 3/1975 | Fiore |
| 3,961,621 A | 6/1976 | Northeved |
| 3,971,385 A | 7/1976 | Corbett |
| 3,994,287 A | 11/1976 | Turp |
| 3,994,301 A | 11/1976 | Agris |
| 4,028,987 A | 6/1977 | Wilson |
| 4,112,932 A | 9/1978 | Chiulli |
| 4,126,291 A | 11/1978 | Gilbert et al. |
| 4,150,929 A | 4/1979 | Brandt |
| 4,168,882 A | 9/1979 | Hopkins |
| 4,180,068 A | 12/1979 | Jacobsen et al. |
| 4,191,191 A | 3/1980 | Auburn |
| 4,222,375 A | 9/1980 | Martinez |
| 4,248,214 A | 2/1981 | Hannah et al. |
| 4,254,762 A | 3/1981 | Yoon |
| 4,269,192 A | 5/1981 | Matsuo |
| 4,274,771 A | 6/1981 | Nishimura |
| 4,285,618 A | 8/1981 | Shanley |
| 4,299,230 A | 11/1981 | Kubota |
| 4,311,138 A | 1/1982 | Sugarman |
| 4,319,563 A | 3/1982 | Kubota |
| 4,356,826 A | 11/1982 | Kubota |
| 4,386,179 A | 5/1983 | Sterling |
| 4,414,966 A | 11/1983 | Stednitz |
| 4,429,856 A | 2/1984 | Jackson |
| 4,436,519 A | 3/1984 | O'Neill |
| 4,493,444 A | 1/1985 | Deli Bon et al. |
| 4,498,902 A | 2/1985 | Ash et al. |
| 4,524,805 A | 6/1985 | Hoffman |
| 4,535,773 A | 8/1985 | Yoon |
| 4,535,808 A | 8/1985 | Johanson et al. |
| 4,537,593 A | 8/1985 | Alchas |
| 4,567,882 A | 2/1986 | Heller |
| 4,601,710 A | 7/1986 | Moll |
| 4,607,619 A | 8/1986 | Seike et al. |
| 4,750,877 A | 6/1988 | McFarlane |
| 4,762,130 A | 8/1988 | Fogarty et al. |
| 4,779,613 A | 10/1988 | Hashiguchi et al. |
| 4,803,999 A | 2/1989 | Liegner |
| 4,813,400 A | 3/1989 | Washizuka et al. |
| 4,850,393 A | 7/1989 | Lashomb |
| 4,895,431 A | 1/1990 | Tsujiuchi et al. |
| 4,901,142 A | 2/1990 | Ikuno et al. |
| 4,956,143 A | 9/1990 | McFarlane |
| 4,959,067 A | 9/1990 | Muller |
| 4,972,827 A | 11/1990 | Kishi et al. |
| 4,978,350 A | 12/1990 | Wagenknecht |
| 5,017,057 A | 5/1991 | Kruygor |
| 5,030,210 A | 7/1991 | Alchas |
| 5,041,100 A | 8/1991 | Rowland et al. |
| 5,057,082 A | 10/1991 | Burchette, Jr. |
| 5,066,288 A | 11/1991 | Deniego et al. |
| 5,098,379 A | 3/1992 | Conway |
| 5,098,388 A | 3/1992 | Kulkashi et al. |
| 5,104,316 A | 4/1992 | Mc Spadden |
| 5,104,388 A | 4/1992 | Quackenbush |
| 5,104,389 A | 4/1992 | Deem et al. |
| 5,114,407 A | 5/1992 | Burbank |
| 5,116,547 A | 5/1992 | Tsukahara et al. |
| 5,144,942 A | 9/1992 | Decarie et al. |
| 5,147,376 A | 9/1992 | Pianetti |
| 5,159,920 A | 11/1992 | Condon et al. |
| 5,163,941 A | 11/1992 | Garth et al. |
| 5,178,186 A | 1/1993 | Levasseur |
| 5,186,972 A | 2/1993 | Williams et al. |
| 5,197,955 A | 3/1993 | Stephens et al. |
| 5,207,656 A | 5/1993 | Kranys |
| 5,217,441 A | 6/1993 | Shichman |
| 5,221,163 A | 6/1993 | Nishimura |
| 5,240,397 A | 8/1993 | Fay et al. |
| 5,246,425 A | 9/1993 | Hunsberger et al. |
| 5,250,068 A | 10/1993 | Ideguchi et al. |
| 5,256,149 A | 10/1993 | Banik et al. |
| 5,258,003 A * | 11/1993 | Ciaglia et al. ................. 606/185 |
| 5,269,316 A | 12/1993 | Spitainy |
| 5,271,380 A | 12/1993 | Riek et al. |
| 5,279,567 A | 1/1994 | Ciaglia et al. |
| 5,288,290 A | 2/1994 | Brody |
| 5,290,276 A | 3/1994 | Sewell |
| 5,290,585 A | 3/1994 | Elton |
| 5,300,033 A | 4/1994 | Miller |
| 5,334,150 A | 8/1994 | Kaali |
| 5,342,382 A | 8/1994 | Brinkerhoff |
| 5,350,364 A | 9/1994 | Stephens et al. |
| 5,366,446 A | 11/1994 | Tal et al. |
| 5,370,624 A | 12/1994 | Edwards et al. |
| 5,372,588 A | 12/1994 | Farley |
| 5,374,253 A | 12/1994 | Burns, Sr. et al. |
| 5,380,291 A | 1/1995 | Kaali |
| 5,387,197 A | 2/1995 | Smith |
| 5,389,077 A | 2/1995 | Melinyshin et al. |
| 5,391,153 A | 2/1995 | Haber et al. |

(56) References Cited

U.S. PATENT DOCUMENTS

| | | |
|---|---|---|
| 5,391,248 A | 2/1995 | Brain |
| 5,392,766 A | 2/1995 | Masterson et al. |
| 5,405,328 A | 4/1995 | Vidal et al. |
| 5,407,427 A | 4/1995 | Zhu et al. |
| 5,431,151 A | 7/1995 | Riek et al. |
| 5,441,041 A | 8/1995 | Sauer et al. |
| 5,443,484 A | 8/1995 | Kirsch et al. |
| 5,445,615 A | 8/1995 | Yoon et al. |
| 5,454,790 A * | 10/1995 | Dubrul .................. 604/104 |
| 5,454,791 A | 10/1995 | Tovey et al. |
| 5,480,410 A | 1/1996 | Cuschieri et al. |
| 5,510,065 A | 4/1996 | McFarlane |
| 5,540,711 A | 7/1996 | Kieturakis et al. |
| 5,542,845 A | 8/1996 | Jenkins |
| 5,549,546 A | 8/1996 | Schneider et al. |
| 5,551,947 A | 9/1996 | Kaai |
| 5,562,696 A | 10/1996 | Nobles et al. |
| 5,569,291 A | 10/1996 | Privitera |
| 5,569,292 A | 10/1996 | Scwemberger et al. |
| 5,577,993 A | 11/1996 | Zhu et al. |
| 5,591,186 A | 1/1997 | Wurster et al. |
| 5,591,192 A | 1/1997 | Privitera et al. |
| 5,593,402 A | 1/1997 | Patrick |
| 5,603,720 A | 2/1997 | Kieturakis |
| 5,609,562 A | 3/1997 | Kaali |
| 5,609,604 A | 3/1997 | Schwemberger et al. |
| 5,613,954 A | 3/1997 | Nelson et al. |
| 5,622,462 A | 4/1997 | Gakhar et al. |
| 5,630,805 A | 5/1997 | Ternamian |
| 5,634,908 A | 6/1997 | Loomas |
| 5,658,236 A | 8/1997 | Sauer |
| 5,662,615 A | 9/1997 | Blake, III |
| 5,662,673 A | 9/1997 | Kieturakis |
| 5,676,611 A | 10/1997 | Foster |
| 5,685,820 A | 11/1997 | Riek et al. |
| 5,695,462 A | 12/1997 | Sutcu et al. |
| 5,697,947 A | 12/1997 | Wolf |
| 5,720,730 A | 2/1998 | Blake, III |
| 5,720,761 A | 2/1998 | Kaali |
| 5,735,867 A | 4/1998 | Golser et al. |
| 5,738,628 A | 4/1998 | Sierocuk |
| 5,743,881 A | 4/1998 | Demco |
| 5,746,734 A | 5/1998 | Domandy, Jr. et al. |
| 5,752,970 A | 5/1998 | Yoon et al. |
| 5,759,185 A | 6/1998 | Grinberg |
| 5,779,697 A | 7/1998 | Glowa et al. |
| 5,785,693 A | 7/1998 | Halninig |
| 5,792,112 A | 8/1998 | Hart et al. |
| 5,797,888 A | 8/1998 | Yoon et al. |
| 5,797,944 A | 8/1998 | Nobeles et al. |
| 5,817,061 A | 10/1998 | Goodwin et al. |
| 5,817,062 A | 10/1998 | Flom et al. |
| 5,836,957 A | 11/1998 | Shulz |
| 5,842,971 A | 12/1998 | Yoon |
| 5,860,996 A | 1/1999 | Urban et al. |
| 5,865,809 A | 2/1999 | Moenning et al. |
| 5,871,474 A | 2/1999 | Hermann et al. |
| 5,876,202 A | 3/1999 | Berlin |
| 5,882,340 A | 3/1999 | Yoon |
| 5,884,639 A | 3/1999 | Chen |
| 5,891,013 A | 4/1999 | Thompson |
| 5,893,865 A | 4/1999 | Swindle |
| 5,904,699 A | 5/1999 | Schwemberger et al. |
| 5,913,818 A | 6/1999 | Co et al. |
| 5,922,351 A | 7/1999 | Daher |
| 5,924,452 A | 7/1999 | Szpapa et al. |
| 5,941,852 A | 8/1999 | Dunlap et al. |
| 5,957,884 A | 9/1999 | Hooven |
| 5,957,888 A | 9/1999 | Hinchliffe |
| 5,968,060 A | 10/1999 | Kellogg |
| 5,976,079 A | 11/1999 | Volz et al. |
| 5,976,168 A | 11/1999 | Chin |
| 5,980,809 A | 11/1999 | Crain et al. |
| 5,984,941 A | 11/1999 | Wilson |
| 6,001,084 A | 12/1999 | Riek |
| 6,007,481 A | 12/1999 | Riek et al. |
| 6,007,544 A | 12/1999 | Kim |
| 6,019,776 A | 2/2000 | Preissman |
| 6,024,551 A | 2/2000 | Yamaguchi |
| 6,030,406 A | 2/2000 | Davis |
| 6,043,310 A | 3/2000 | Liu et al. |
| 6,053,194 A | 4/2000 | Nelson et al. |
| 6,068,637 A | 5/2000 | Popov et al. |
| 6,077,481 A | 6/2000 | Ichida et al. |
| 6,092,551 A | 7/2000 | Bennett |
| 6,168,355 B1 | 1/2001 | Wardell |
| 6,179,528 B1 | 1/2001 | Wardell |
| 6,203,559 B1 | 3/2001 | Davis |
| 6,203,745 B1 | 3/2001 | Wachsmann et al. |
| 6,221,061 B1 | 4/2001 | Engelson et al. |
| 6,228,059 B1 | 5/2001 | Astarita |
| 6,228,063 B1 | 5/2001 | Aboul-Hosn |
| 6,270,484 B1 | 8/2001 | Yoon |
| 6,302,873 B1 | 10/2001 | Moenning |
| 6,319,266 B1 | 11/2001 | Stellon |
| 6,346,074 B1 | 2/2002 | Roth |
| 6,355,014 B1 | 3/2002 | Zadno-Azizi et al. |
| 6,387,043 B1 | 5/2002 | Yoon |
| 6,462,111 B1 | 10/2002 | Singh et al. |
| 6,468,228 B1 | 10/2002 | Topel et al. |
| 6,478,806 B2 | 11/2002 | McFarlane |
| 6,508,759 B1 | 1/2003 | Taylor et al. |
| 6,520,939 B2 | 2/2003 | Lafontaine |
| 6,579,298 B1 | 6/2003 | Bruneau et al. |
| 6,656,160 B1 | 12/2003 | Taylor et al. |
| 6,656,198 B2 | 12/2003 | Tsonton et al. |
| 6,685,630 B2 | 2/2004 | Sauer et al. |
| 6,764,107 B1 | 7/2004 | Obahi et al. |
| 6,770,731 B2 | 8/2004 | Mason et al. |
| 6,835,201 B2 | 12/2004 | O'Heeron |
| 6,884,253 B1 | 4/2005 | McFarlane |
| 6,887,194 B2 | 5/2005 | Hart et al. |
| 6,902,541 B2 | 6/2005 | McNally et al. |
| 6,939,296 B2 | 9/2005 | Ewers et al. |
| 7,008,979 B2 | 3/2006 | Schottman et al. |
| 7,037,303 B2 | 5/2006 | Beaufore et al. |
| 7,056,294 B2 | 6/2006 | Khairkhahan et al. |
| 7,056,329 B2 | 6/2006 | Kerr |
| 7,070,586 B2 | 7/2006 | Hart et al. |
| 7,182,752 B2 | 2/2007 | Stubbs |
| 7,344,519 B2 | 3/2008 | Wing et al. |
| 7,370,709 B2 | 5/2008 | Williamson, Jr. |
| 7,470,255 B2 | 12/2008 | Sterns et al. |
| 7,563,250 B2 | 7/2009 | Wenchell |
| 7,686,823 B2 | 3/2010 | Pingleton et al. |
| 7,708,713 B2 | 5/2010 | Albrecht et al. |
| 7,758,603 B2 * | 7/2010 | Taylor et al. .................. 606/185 |
| 7,794,644 B2 | 9/2010 | Taylor et al. |
| 7,811,253 B2 | 10/2010 | Hart et al. |
| 7,942,862 B2 | 5/2011 | Hart et al. |
| 7,947,058 B2 | 5/2011 | Kahle et al. |
| 8,007,477 B2 | 8/2011 | Johnson et al. |
| 8,028,395 B2 | 10/2011 | Taylor et al. |
| 8,075,530 B2 | 12/2011 | Taylor et al. |
| 8,105,285 B2 | 1/2012 | Hart et al. |
| 8,128,590 B2 | 3/2012 | Albrecht et al. |
| 8,152,828 B2 * | 4/2012 | Taylor et al. .................. 606/190 |
| 8,267,952 B2 | 9/2012 | Kahle et al. |
| 8,282,663 B2 | 10/2012 | Smith |
| 8,292,853 B2 | 10/2012 | Hart et al. |
| 8,317,815 B2 | 11/2012 | Mastri et al. |
| 8,377,090 B2 | 2/2013 | Taylor et al. |
| 8,382,663 B2 | 2/2013 | Taylor |
| 8,608,768 B2 * | 12/2013 | Taylor et al. .................. 606/190 |
| 2002/0013597 A1 | 1/2002 | McFarlane |
| 2002/0026207 A1 | 2/2002 | Stellon et al. |
| 2002/0133188 A1 | 9/2002 | O'Heeron et al. |
| 2002/0183715 A1 | 12/2002 | Mantell et al. |
| 2002/0183775 A1 * | 12/2002 | Tsonton et al. .................. 606/185 |
| 2003/0023201 A1 | 1/2003 | Aboul-Hosn |
| 2003/0032755 A1 | 2/2003 | Gomey et al. |
| 2003/0059263 A1 | 3/2003 | Chen |
| 2003/0187471 A1 | 10/2003 | Cooper |
| 2004/0015185 A1 | 1/2004 | Ewers et al. |

(56) References Cited

U.S. PATENT DOCUMENTS

| | | | |
|---|---|---|---|
| 2004/0082969 A1 | 4/2004 | Kerr | |
| 2004/0093000 A1 | 5/2004 | Kerr | |
| 2004/0093018 A1 | 5/2004 | Johnson et al. | |
| 2004/0106942 A1 | 6/2004 | Taylor et al. | |
| 2004/0108623 A1 | 6/2004 | Deeter et al. | |
| 2004/0167559 A1 | 8/2004 | Taylor et al. | |
| 2004/0199127 A1 | 10/2004 | Jensen et al. | |
| 2004/0204671 A1 | 10/2004 | Stubbs et al. | |
| 2004/0230155 A1 | 11/2004 | Blanco et al. | |
| 2004/0230217 A1 | 11/2004 | O'Heeroon | |
| 2004/0254517 A1 | 12/2004 | Quiroz-Mercado et al. | |
| 2005/0033237 A1 | 2/2005 | Fentress et al. | |
| 2005/0033246 A1 | 2/2005 | Ahlberg et al. | |
| 2005/0038466 A1 | 2/2005 | O'Heeron et al. | |
| 2005/0059865 A1 | 3/2005 | Kahle | |
| 2005/0065543 A1 | 3/2005 | Kahle et al. | |
| 2005/0070850 A1 | 3/2005 | Albrecht | |
| 2005/0107803 A1 | 5/2005 | Guanche | |
| 2005/0107816 A1 | 5/2005 | Pingleton et al. | |
| 2005/0113533 A1 | 5/2005 | Shaikh et al. | |
| 2005/0149094 A1 | 7/2005 | Kashara et al. | |
| 2005/0149096 A1 | 7/2005 | Hilal et al. | |
| 2005/0159711 A1 | 7/2005 | Kathrani et al. | |
| 2005/0216028 A1 | 9/2005 | Hart et al. | |
| 2005/0227610 A1 | 10/2005 | Zukor et al. | |
| 2005/0273133 A1 | 12/2005 | Schluzas et al. | |
| 2005/0283122 A1 | 12/2005 | Nordgren | |
| 2005/0288622 A1 | 12/2005 | Albrecht et al. | |
| 2006/0030755 A1 | 2/2006 | Ewers et al. | |
| 2006/0030870 A1 | 2/2006 | Staudner | |
| 2006/0041270 A1 | 2/2006 | Lenker et al. | |
| 2006/0047284 A1 | 3/2006 | Gresham | |
| 2006/0058570 A1 | 3/2006 | Rapach et al. | |
| 2006/0074374 A1 | 4/2006 | Gresham | |
| 2006/0118189 A1 | 6/2006 | Trekulve et al. | |
| 2006/0224174 A1 | 10/2006 | Smith et al. | |
| 2006/0264991 A1 | 11/2006 | Johnson | |
| 2007/0027453 A1 | 2/2007 | Hart et al. | |
| 2007/0075465 A1 | 4/2007 | Taylor et al. | |
| 2007/0088277 A1 | 4/2007 | McGinley | |
| 2007/0239108 A1 | 10/2007 | Albrecht et al. | |
| 2008/0065021 A1 | 3/2008 | Jenkins et al. | |
| 2008/0086074 A1 | 4/2008 | Taylor et al. | |
| 2008/0086093 A1 | 4/2008 | Steppe et al. | |
| 2009/0030375 A1 | 1/2009 | Franer et al. | |
| 2009/0137943 A1 | 5/2009 | Stearns et al. | |
| 2009/0187079 A1 | 7/2009 | Albrecht et al. | |
| 2009/0281500 A1 | 11/2009 | Acosta et al. | |
| 2010/0025045 A1 | 2/2010 | Lake et al. | |
| 2010/0298776 A1* | 11/2010 | Taylor et al. | 604/170.02 |

FOREIGN PATENT DOCUMENTS

| | | |
|---|---|---|
| DE | 0365049 | 12/1922 |
| DE | 1616107 | 4/1971 |
| DE | 2218901 | 10/1973 |
| DE | 2538758 | 3/1977 |
| DE | 2929233 | 1/1980 |
| DE | 2922239 | 12/1980 |
| DE | 4020956 | 1/1991 |
| DE | 4133073 | 4/1992 |
| DE | 4035146 | 5/1992 |
| DE | 4116648 | 11/1992 |
| DE | 29503750 | 4/1995 |
| DE | 29521431 | 4/1997 |
| DE | 19541041 | 5/1997 |
| DE | 19718086 | 11/1998 |
| DE | 19819432 | 11/1999 |
| EP | 0135364 | 3/1985 |
| EP | 0312787 | 4/1989 |
| EP | 0347140 | 12/1989 |
| EP | 0369936 | 5/1990 |
| EP | 0369937 | 5/1990 |
| EP | 0474124 | 3/1992 |
| EP | 0548612 | 6/1993 |
| EP | 0556056 | 8/1993 |
| EP | 0664992 | 8/1995 |
| EP | 0724864 | 8/1996 |
| EP | 1074224 | 2/2001 |
| EP | 1582158 | 10/2005 |
| EP | 2229897 | 9/2010 |
| EP | 2233090 | 9/2010 |
| FR | 1370580 | 8/1964 |
| GB | 2 124 970 | 2/1984 |
| GB | 186 005 | 9/1992 |
| GB | 2 313 316 | 11/1997 |
| JP | 408127661 | 5/1996 |
| JP | 2001-137253 | 5/2001 |
| SU | 0942730 | 7/1982 |
| SU | 1328658 | 8/1987 |
| SU | 1329769 | 8/1987 |
| WO | WO 93/25148 | 12/1993 |
| WO | WO 98/33536 | 2/1994 |
| WO | WO 94/11040 | 5/1994 |
| WO | WO 96/01074 A2 | 1/1996 |
| WO | WO 96/01132 | 1/1996 |
| WO | WO 96/10361 | 4/1996 |
| WO | WO 97/40758 | 11/1997 |
| WO | WO 99/02089 | 1/1999 |
| WO | WO 99/15084 | 4/1999 |
| WO | WO 00/18306 | 4/2000 |
| WO | WO 00/54648 | 9/2000 |
| WO | WO 01/01847 | 1/2001 |
| WO | WO 01/01871 | 1/2001 |
| WO | WO 02/01998 | 1/2002 |
| WO | WO 01/08563 | 2/2002 |
| WO | WO 02/34108 | 5/2002 |
| WO | WO 02/41795 | 5/2002 |
| WO | WO 03/026512 | 4/2003 |
| WO | WO 03/032819 | 4/2003 |
| WO | WO 03/096879 | 11/2003 |
| WO | WO 2004/037097 | 5/2004 |
| WO | WO 2004/093699 | 11/2004 |
| WO | WO 2005/063134 | 7/2005 |
| WO | WO 2007/093957 | 8/2007 |

OTHER PUBLICATIONS

Co-Pending U.S. Appl. No. 12/750,372, filed Mar. 30, 2010, title: "Bladeless Obturator".
Co-Pending U.S. Appl. No. 11/549,872, filed Oct. 16, 2006, title: "Surgical Devices, Systems and Methods Thereof Having Gel Material, Gel Coatings, or Gel Lubricants".
Co-Pending U.S. Appl. No. 13/565,972, filed Aug. 3, 2012, title: "Bladeless Optical Obturator".
Co-Pending U.S. Appl. No. 13/356,260, filed Jan. 23, 2012, title: "Insufflating Optical Surgical Instrument".
Co-Pending U.S. Appl. No. 13/078,750, filed Apr. 1, 2011 title "Surgical Access Apparatus and Method".
Co-Pending U.S. Appl. No. 12/569,652, filed Sep. 29, 2009; title "First-Entry Trocar System".
Co-Pending U.S. Appl. No. 12/359,964, filed Jan. 26, 2009, title: "Insufflating Access System".
Co-Pending U.S. Appl. No. 13/462,330, filed May 2, 2012, title: "Low-Profile Surgical Universal Access Port".
Co-Pending U.S. Appl. No. 13/411,244, filed Mar. 2, 2012, title: "Blunt Tip Obturator".
Co-Pending U.S. Appl. No. 13/586,825, filed Aug. 15, 2012, title: "Blunt Tip Obturator".
Co-Pending U.S. Appl. No. 11/868,883, filed Oct. 8, 2007; Title: "Visual Insufflation Port".
International Bureau of WIPO, International Preliminary Report on Patentability for International Application No. PCT/US04/032346, dated May 20, 2008.
International Bureau of WIPO, International Preliminary Report on Patentability for International Application No. PCT/US2005/022716 mailed Nov. 22, 2005.
International Bureau of WIPO, International Preliminary Report on Patentability for International Application No. PCT/US2006/060013, mailed Apr. 24, 2008.

(56) References Cited

OTHER PUBLICATIONS

International Bureau of WIPO, The International Preliminary Report on Patentability for International Application No. PCT/US2009/058792, titled First Entry Trocar System, dated Mar. 29, 2011.
International Bureau of WIPO, The International Preliminary Report on Patentability for International Application No. PCT/US2007/080724, titled "Visual Insufflation Port", dated Apr. 7, 2009.
International Bureau of WIPO, The International Preliminary Report on Patentability for International Application No. PCT/US2009/32026, titled "Insufflating Access System", dated Jul. 27, 2010.
International Bureau of WIPO, The International Preliminary Report on Patentability for International Application No. PCT/US2004/000695, titled "Surgical Access Apparatus and Method", dated Jul. 22, 2005.
International Bureau of WIPO, The International Preliminary Report on Patentability for International Application No. PCT/US2004/04883, titled "Surgical Access Apparatus and Method", dated Sep. 9, 2005.
International Searching Authority, International Search Report and Written Opinion for International Application No. PCT/US2004/000695, titled "Surgical Access Apparatus and Method", mailed Jan. 12, 2005.
International Searching Authority, International Search Report and Written Opinion for International Application No. PCT/US2004/04883, titled "Surgical Access Apparatus and Method", mailed Mar. 31, 2005.
International Searching Authority, International Search Report and Written Opinion for International Application No. PCT/US2002/06759, titled "Bladeless Obturator", mailed Jul. 12, 2002.
International Searching Authority, International Search Report and Written Opinion for International Application No. PCT/US2005/022716, titled "Insufflating Optical Surgical Instrument", mailed Nov. 22, 2005.
International Searching Authority, International Search Report and Written Opinion for International Application No. PCT/US04/32346, titled Bladeless Optical Obturator, mailed May 20, 2008.
International Searching Authority, International Search Report and Written Opinion for International Application No. PCT/US2009/32026, titled "Insufflating Access System", mailed Mar. 23, 2009.
International Searching Authority, International Search Report and Written Opinion for International Application No. PCT/US2007/080724, titled "Visual Insufflation Port", mailed Apr. 16, 2008.
International Searching Authority/US, International Search Report and the Written Opinion of the International Searching Authority dated May 27, 2009, for International Application No. PCT/US2009/037863, titled "Instrument Seal with Inverting Shroud", mailed May 27, 2009.
The International Searching Authority, The International Search Report and the Written Opinion for International Application No. PCT/US2009/058792, titled "First Entry Trocar System", mailed Dec. 23, 2009.
International Searching Authority, International Search Report and Written Opinion for International Application No. PCT/US2012/036119, title "Low-Profile Surgical Universal Access Port", mailed Nov. 7, 2012.
European Patent Office, Supplementary European Search Report for European Patent Application No. EP 04 70 1731 based on International Application No. PCT/US2004/000695, titled "Surgical Access Apparatus and Method", dated Apr. 11, 2007.
European Patent Office, Supplementary European Search Report for European Patent Application No. EP 02706494.8, titled "Bladeless Obturator", dated Jun. 24, 2008.
European Patent Office, Supplementary European Search Report for European Patent Application No. EP 03753017.7, titled "Blunt Tip Obturator", dated Nov. 21, 2008.
European Patent Office, Supplementary European Search Report for European Patent Application No. EP 04712378, titled "Surgical Access Apparatus and Method", dated May 19, 2008.
European Patent Office, Supplementary European Search Report for European Patent Application No. EP 07843973.4, titled "Visual Insufflation Port" dated Oct. 4, 2008.
European Patent Office, Supplementary European Search Report for European Patent Application No. EP 04793965.7, titled "Bladeless Optical Obturator", dated Apr. 16, 2010.
European Patent Office, Supplementary European Search Report for European Patent Application No. EP 11154547.1, titled "Blunt Tip Obturator", dated Mar. 22, 2011.
European Patent Office, European Search Report for European Application No. 11191191.3, titled "Bladeless Obturator" dated Feb. 29, 2012.
European Patent Office, European Search Report for European Application No. 11191179.8, titled "Bladeless Obturator", dated Feb. 21, 2012.
European Patent Office, European Search Report for European Application No. 11191193.9, titled "Bladeless Obturator", dated Mar. 5, 2012.
European Patent Office, European Search Report for European Application No. 11191187.1, titled Bladeless Obturator, dated Feb. 23, 2012.
European Patent Office, European Search Report for European Application No. 11191184.8, titled "Bladeless Obturator", dated Feb. 23, 2012.
European Patent Office, European Search Report for European Application No. 11191189.7, titled "Bladeless Obturator", dated Feb. 24, 2012.
European Patent Office, European Search Report for European Application No. 11191175.6, titled "Bladeless Obturator", dated Feb. 21, 2012.
European Patent Office, European Search Report for European Application No. 047017314, titled "Surgical Access Apparatus and Method", dated Mar. 30, 2007.
Taut, Inc., ADAPT—Asymmetrical Dilating Access Port, Geneva Illinois.
Karl Storz, The Karl Storz Ternamian EndoTIP (TM) System, date: Aug. 27, 2001.
Karl Storz, Zerocart Trocar with eccentric tip, Recklinghausen, Germany, date Mar. 7, 2001.
Ethicon Endo-Surgery, Inc., Endopath Minimally Invasive Access, date: 2001.
European Patent Office, Invitation to Pay Additional Fees for International Application No. PCT/US2012/036119, titled "Low-Profile Surgical Universal Access Port", mailed Jul. 13, 2012.
European Patent Office, European Search Report for European Application No. 12187933, titled "Insufflating Optical Surgical Instrument", dated Nov. 20, 2012.
European Patent Office, European Search Report for European Application No. 12187929, titled "Insufflating Optical Surgical Instrument", dated Nov. 20, 2012.
European Patent Office, European Search Report for European Application No. 12186716.2, titled "Bladeless Optical Obturator", dated Mar. 7, 2013.
European Patent Office, European Search Report for European Application No. 12186717.0, titled "Bladeless Optical Obturator", dated Mar. 7, 2013.
European Patent Office, European Search Report for European Application No. 12186712.1, titled "Bladeless Optical Obturator", dated Mar. 7, 2013.
European Patent Office, European Search Report for European Application No. 12186720.4, titled "Bladeless Optical Obturator", dated Mar. 7, 2013.
International Searching Authority, International Search Report and Written Opinion for International Application No. PCT/US2013/023458 titled "Adaptable Obturator for Various Sized Trocars", mailed Mar. 19, 2013.
European Patent Office, European Search Report for European Application No. 12186722.0, titled "Bladeless Optical Obturator", dated Mar. 20, 2013.

(56) References Cited

OTHER PUBLICATIONS

European Patent Office, European Search Report for European Application No. 12186721.2, titled "Bladeless Optical Obturator", dated Mar. 22, 2013.
European Patent Office, European Search Report for European Application No. 12186723.8, titled "Bladeless Optical Obturator", dated Mar. 22, 2013.
European Patent Office, European Communication pursuant to Article 94(3) EPC for European Patent Application No. 12186717 .0, titled "Bladeless Optical Obturator", dated Mar. 26, 2013.
Yang, Guoqing, Hong Jun, Zhu, Linbo, Li Baotong, Xiong Meihua, and Wang Fei, Chinese Journal of Mechanical Engineering, (vol. 26, No. 3, 2013), Three-Dimensional Finite Element Analysis of the Mechanical Properties of Helical Threat Connection, Revised Jan. 28, 2013.

* cited by examiner

BLUNT TIP OBTURATOR

CROSS-REFERENCE TO RELATED APPLICATIONS

This application is a continuation of U.S. patent application Ser. No. 13/411,244 filed on Mar. 2, 2012, now U.S. Pat. No. 8,608,768, which is a continuation of U.S. patent application Ser. No. 12/836,023 filed on Jul. 14, 2010, now U.S. Pat. No. 8,152,828, which is a continuation of U.S. patent application Ser. No. 10/514,313, now U.S. Pat. No. 7,758,603, which entered the U.S. National Phase on Nov. 12, 2004 from International Application No. PCT/2003/014924, filed May 13, 2003, which published in English as International Patent Publication WO 2003/096879 A3, which claims the benefit of U.S. Provisional Patent Application No. 60/381,469, filed May 16, 2002; the disclosures of all of these applications and patents are incorporated by reference in their entireties herein.

FIELD OF THE INVENTION

This invention generally relates to trocar systems including obturators and, more specifically, to blunt cone tip obturators.

BACKGROUND

Trocar systems have been of particular advantage in facilitating less invasive surgery across a body wall and within a body cavity. This is particularly true in the case of the abdominal surgery where trocars have provided working channels across the abdominal wall to facilitate the use of instruments within the abdominal cavity.

The trocar systems of the past typically include a cannula, which defines the working channel, and an obturator which is used to place the cannula across the abdominal wall. The obturator is inserted into the working channel of the cannula and then pushed through the abdominal wall with a penetration force of sufficient magnitude to result in penetration of the abdominal wall. Once the cannula is in place, the obturator can be removed.

In the past, obturators have been developed with an intent to provide a reduction in the force required for penetration. Sharp blades have typically been used to enable the obturator to cut its way through the abdominal wall. While the blades have facilitated a reduced penetration force, they have been of particular concern once the abdominal wall has been penetrated. Within the abdominal cavity, there are organs which need to be protected against any puncture by an obturator.

In some cases, shields have been provided with the obturators in order to sense penetration of the abdominal wall and immediately shield the sharp blades. These shielding systems have been very complex, have required a large amount of time to deploy, and have generally been ineffective in protecting the organs against the sharp blades.

Blunt-tip obturators have been contemplated with both symmetrical and asymmetrical designs. While the blunt tip tends to inhibit damage to interior organs, it also tends to increase the penetration force associated with the obturator. Thus, there is a need in the art for an improved bladeless obturator that reduces the force required to place the obturator across the abdominal wall.

SUMMARY

In accordance with the present invention, a blunt tip obturator similar to that described in international application No. PCT/US02/06759 further including a cone at its distal tip is disclosed with characteristics that reduce the force required to penetrate the abdominal wall. The addition of the cone also reduces the tendency for the abdominal wall and the peritoneum to deflect or "tent" during insertion of the obturator. The blunt cone tip obturator of the invention penetrates and twists radially from a distal end to a proximal end of the tip. The blunt cone tip obturator facilitates insertion with a reduced penetration force as the user moves the tip back and forth radially while applying an axial penetration force. The blunt cone tip obturator can be directed and inserted between the fibers and then rotated to provide increased penetration and fiber separation.

These and other features and advantages of the invention will become more apparent with a discussion of preferred embodiments in reference to the associated drawings.

DETAILED DESCRIPTION OF THE INVENTION

Figure 1:
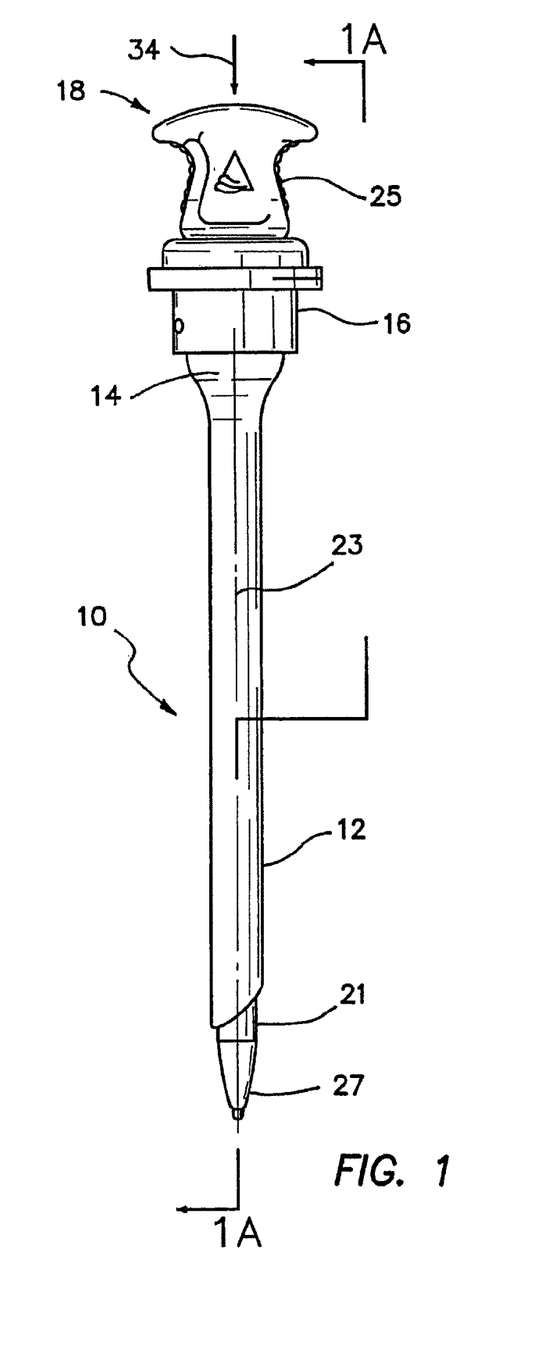
FIG. 1 illustrates a side view of a trocar system including a cannula with associated valve housing, and an obturator with a blunt cone tip extending through the working channel of the cannula to facilitate placement across the abdominal wall according to the present invention.
Figure 1A:
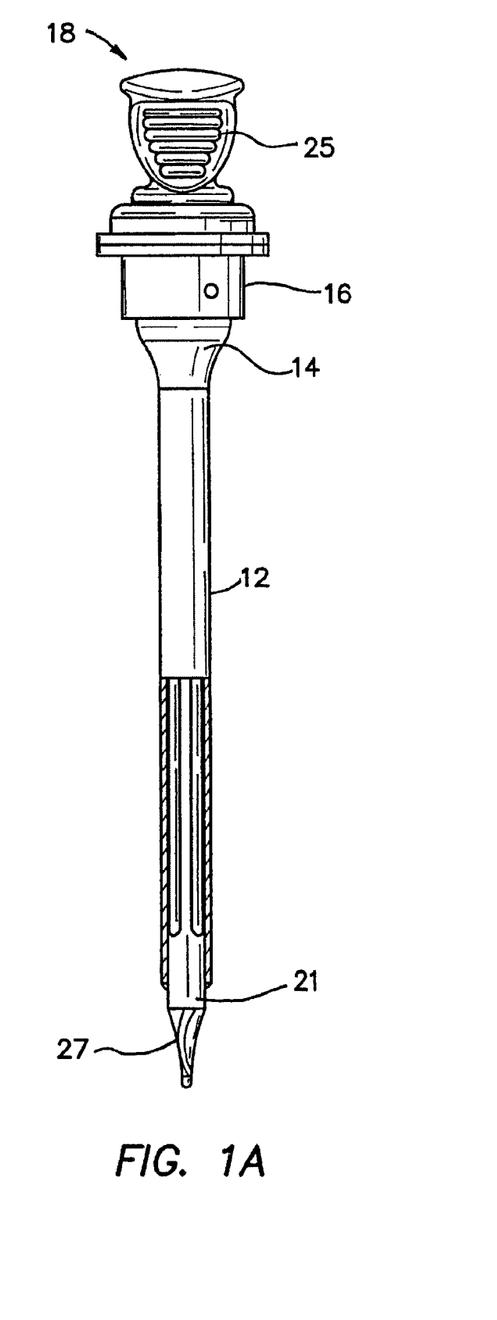
FIG. 1A illustrates a side sectional view taken along line 1A-1A of of the trocar system FIG. 1 according to the present invention.

A trocar system is illustrated in FIGS. 1 and 1A and is designated by reference numeral 10. This system includes a cannula 12, defining a working channel 14, and a valve housing 16. The system 10 also includes an obturator 18 having a shaft 21 extending along an axis 23. A handle 25 is disposed at a proximal end of the shaft at 21 while a blunt cone tip 27 is disposed at a distal end of the shaft 21. The shaft 21 of the obturator 18 is sized and configured for disposition within the working channel 14 of the cannula 12. With this disposition, the obturator 18 can be directed to penetrate a body wall such as the abdominal wall to provide the cannula 12 with access across the wall and into a body cavity, such as the peritoneal or abdominal cavity. The blunt cone tip 27 serves to direct the obturator 18 through the abdominal wall and the peritoneum, and can be removed with the obturator 18 once the cannula 12 is operatively disposed with the working channel 14 extending into the abdominal cavity.

In order to facilitate penetration of the abdominal wall by the trocar system 10, a penetration force, represented by an arrow 34, is typically applied along the axis 23. It can be appreciated that the force required to penetrate the abdominal wall drops significantly once the wall is penetrated. Further application of the force 34, even for an instant of time, can result in injury to organs within the cavity. Where the obturators of the past have included blades facilitating penetration of the abdominal wall, these blades have been particularly threatening and detrimental to the interior organs.

Consequently, in accordance with the present invention, the tip 27 is provided with a blunt cone configuration. Blunt tips have been used in the past to reduce any potential for damage to interior organs. However, these blunt tips have increased the amount of force 34 required for penetration of the abdominal wall. The blunt cone tip 27 of the present invention takes into account the anatomical configuration of the abdominal wall with an improved structural design and method of insertion.

To fully appreciate these aspects of this invention, it is helpful to initially discuss the anatomy associated with the abdominal wall. The abdominal wall typically includes a skin layer and a series of muscle layers. The muscle layers are each defined by muscle fibers that extend generally parallel to each other in a direction that is different for each of the layers. For example, fibers of a first muscle layer and a second muscle layer may extend in directions that are 45 degrees off of each other.

Having noted the directional nature of the muscle fibers, it can be appreciated that such a structure is most easily penetrated by an obturator having a blunt cone tip. The blunt cone tip also has a rectangular and twisted configuration so as to provide better movement between the muscle layers. That is, the blunt cone tip is capable of being moved generally parallel to and between the fibers associated with a particular muscle layer. As a result, the obturator of the present invention reduces the penetration force 34 required to push the obturator 18 through a particular layer.

As described earlier, the fibers of the muscle layers may be oriented at different angles to each other such that proper alignment of the tip 27 for penetration of one layer may not necessarily result in proper alignment for penetration of the next layer. For at least this reason, the obturator 18 has a blunt cone tip 27 to direct the obturator 18 through the different layers and a rectangular configuration that is twisted slightly so that penetration of a first layer begins to rotate the distal end of the blunt cone tip 27 into proper orientation for penetration of the next layer.

The twisted configuration of the blunt cone tip 27 also causes the blunt cone tip 27 to function with the mechanical advantage of a screw thread. With this configuration, a preferred method of placement requires that the user grip the handle 25 of the obturator 18 and twist it about the axis 23. This twisting motion in combination with the screw configuration of the blunt cone tip 27 converts radial movement into forward movement along the axis 23. Thus, the user applies both a forwardly directed force as well as a radial force to move the trocar system 10 in a forward direction. Since all of the force supplied by the user is not directed axially along the arrow 34, this concept avoids the tendency of prior trocar systems to jump forward upon penetration of the abdominal wall.

Figure 2:
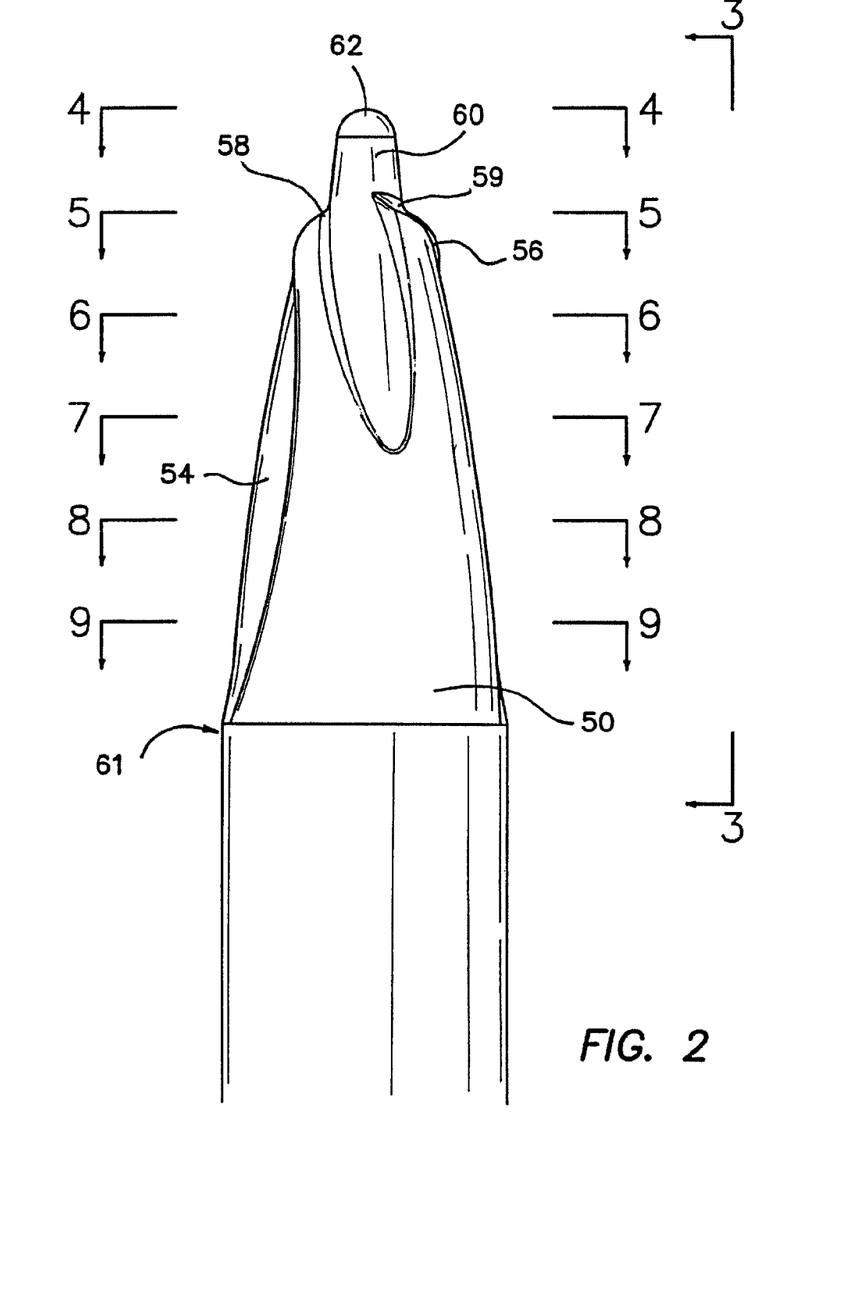
FIG. 2 is a side elevation view of the blunt cone tip of a preferred embodiment of the invention.
Figure 3:
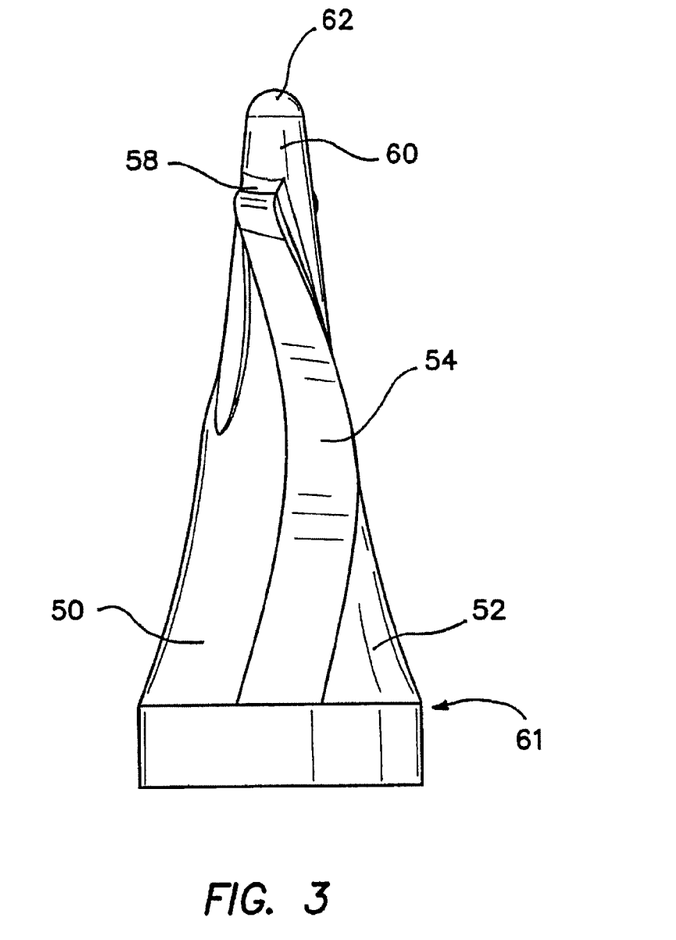
FIG. 3 is a side elevation view of the blunt cone tip taken along line 3-3 of FIG. 2 according to the present invention.

The twisted configuration of the blunt cone tip 27 is most apparent in the side elevation views of FIGS. 2 and 3. In this embodiment, the blunt cone tip 27 comprises generally of eight surfaces: two opposing surfaces 50 and 52, separated by two side surfaces 54 and 56, two end surfaces 58 and 59, a conical surface 60 formed in surfaces 50 and 52 around axis 23 and extending beyond end surfaces 58 and 59, and a blunt surface 62. A plane drawn through the axis 23 would show the tip 27 to be composed of two symmetrical halves.

Figures 4, 5, 6:
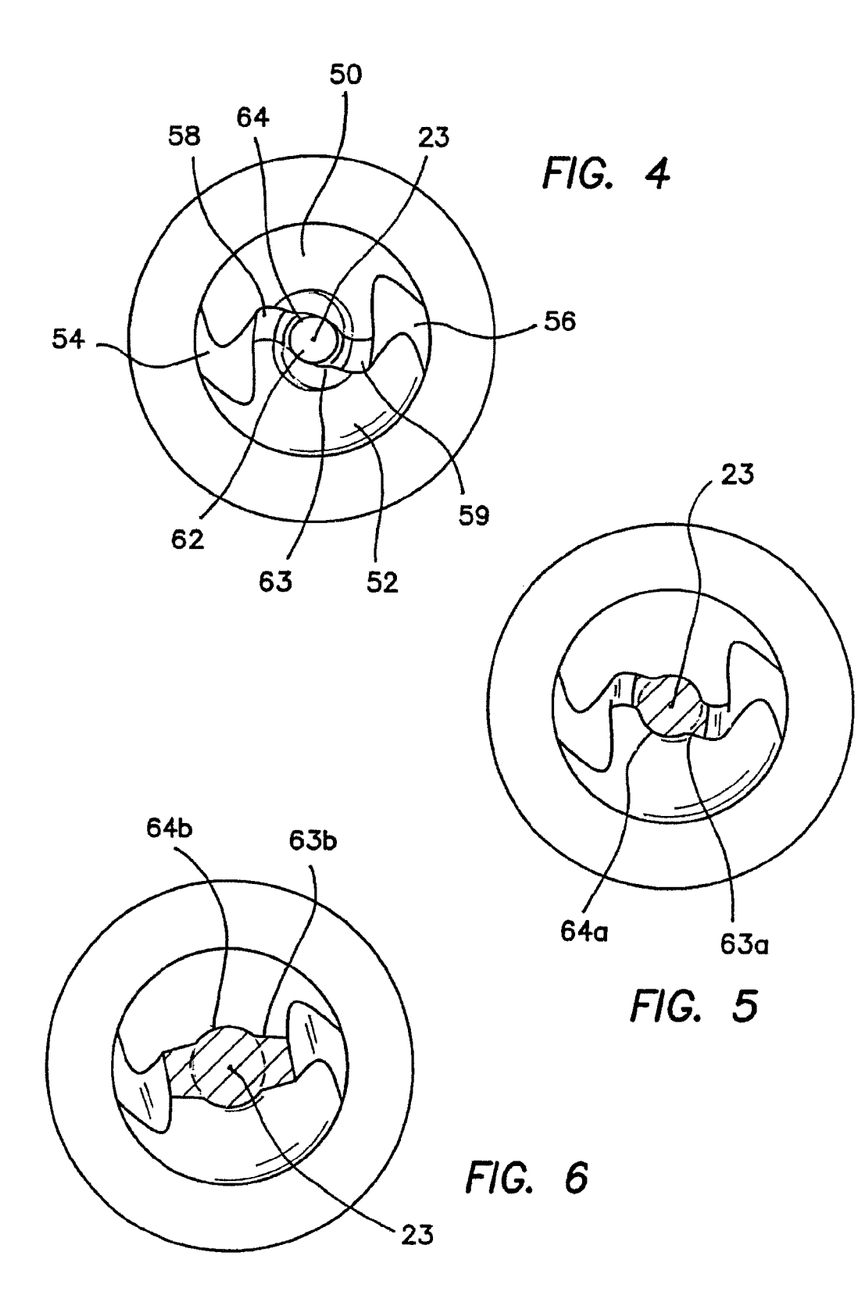
FIG. 4 is an end view taken along line 4-4 of the blunt cone tip of FIG. 2 according to the present invention.
FIG. 5 is a radial cross-section view taken along line 5-5 of the blunt cone tip of FIG. 2 according to the present invention.
FIG. 6 is a radial cross-section view taken along line 6-6 of the blunt cone tip of FIG. 2 according to the present invention.

The surfaces 50 and 52, side surfaces 54 and 56, and conical surface 60 generally define the cross section of the blunt cone tip 27 from blunt surface 62 to proximal end 61. This configuration can best be appreciated with reference to the cross section views of FIGS. 4-9. In FIG. 4, the distal end of the blunt cone tip 27 is shown with a circle 64 having the smallest circular area and a rectangle 63 having the greatest length-to-width ratio. The rectangle 63 has a twisted, S-shaped configuration at end surfaces 58 and 59.

Figures 7, 8, 9:
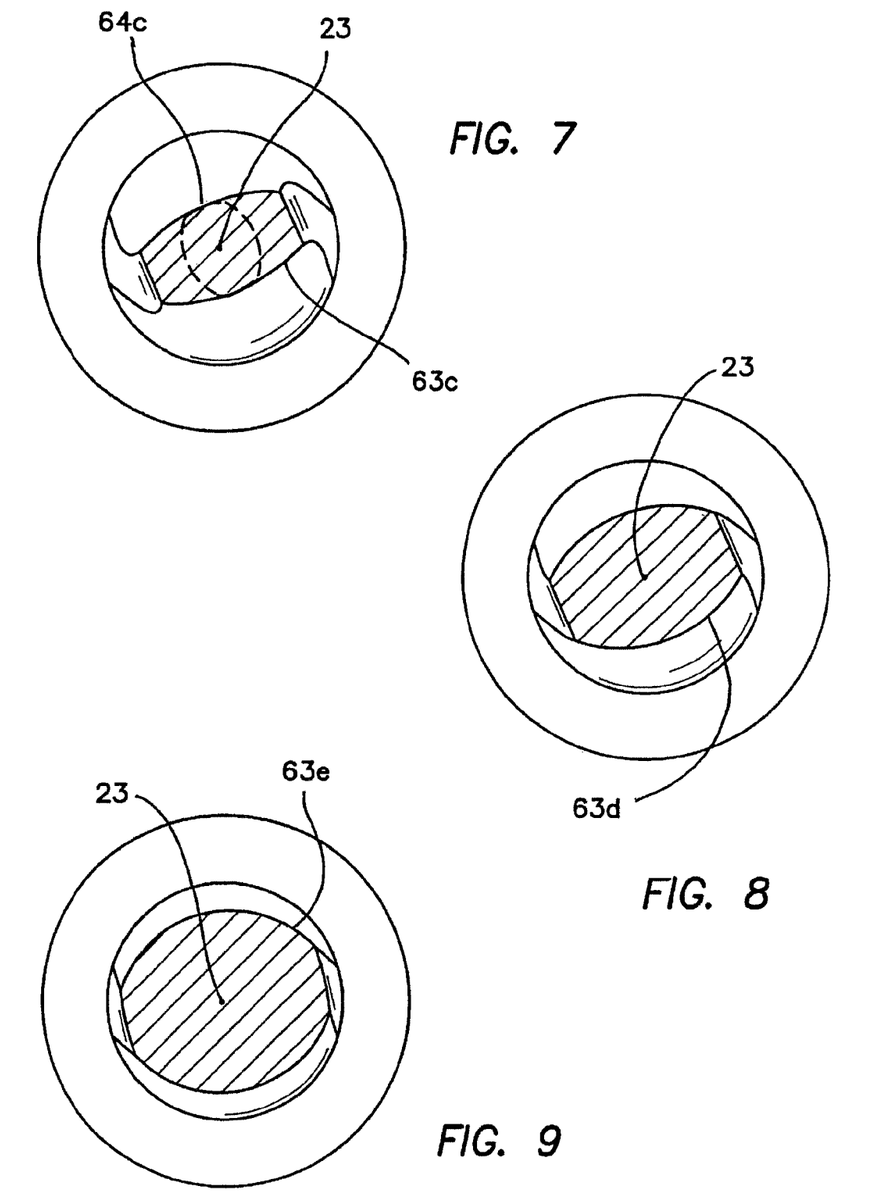
FIG. 7 is a radial cross-section view taken along line 7-7 of the blunt cone tip of FIG. 2 according to the present invention.
FIG. 8 is a radial cross-section view taken along line 8-8 of the blunt cone tip of FIG. 2 according to the present invention.
FIG. 9 is a radial cross-section view taken along line 9-9 of the blunt cone tip of FIG. 2 according to the present invention.

As views are taken along progressive proximal cross sections, it can be seen that the circle 64 becomes larger and the rectangle 63 becomes less twisted, and the width increases relative to the length of the rectangle 63. The spiral nature of the blunt cone tip 27 is also apparent as the circle 64 and rectangle 63 move counterclockwise around the axis 23. This is perhaps best appreciated in a comparison of the circle 64 and the rectangle 63 in FIG. 6 relative to that in FIG. 5. With progressive proximal positions, the circle 64 begins to expand with increasing circular area and the rectangle 63 begins to widen with a reduction in the ratio of length to width. The long sides of the rectangle 63 also tend to become more arcuate as they approach a more rounded configuration most apparent in FIGS. 8 and 9. That is, the circle 64 and the rounded rectangle 63 become more concentric with progressive proximal positions. Furthermore, the circle 64 expands at a lesser rate than the rectangle 63, which eventually absorbs the circle 64 as shown in FIGS. 8 and 9. In these figures, it will also be apparent that the rotation of the rectangle 63 reaches a most counterclockwise position and then begins to move clockwise. This is best illustrated in FIGS. 7-9. This back and forth rotation results from the configuration of the side surfaces 54 and 56, which in general are U-shaped as best illustrated in FIGS. 2 and 3.

The ratio of the length to width of the rectangle 63 is dependent on the configuration of the side surfaces 54 and 56, which define the short sides of the rectangle 63 as well as the configuration of the surfaces 50 and 52, which define the long sides of the rectangle 63. Again with reference to FIGS. 2 and 3, it can be seen that the side surfaces 54 and 56 are most narrow at the end surfaces 58 and 59. As the side surfaces 54 and 56 extend proximally, they reach a maximum width near the point of the most counterclockwise rotation, shown generally in FIG. 8, and then reduce in width as they approach the proximal end 61. Along this same distal to proximal path, the surfaces 50 and 52 transition from a generally flat configuration at the end surfaces 58 and 59 to a generally rounded configuration at the proximal end 61.

Figure 10:
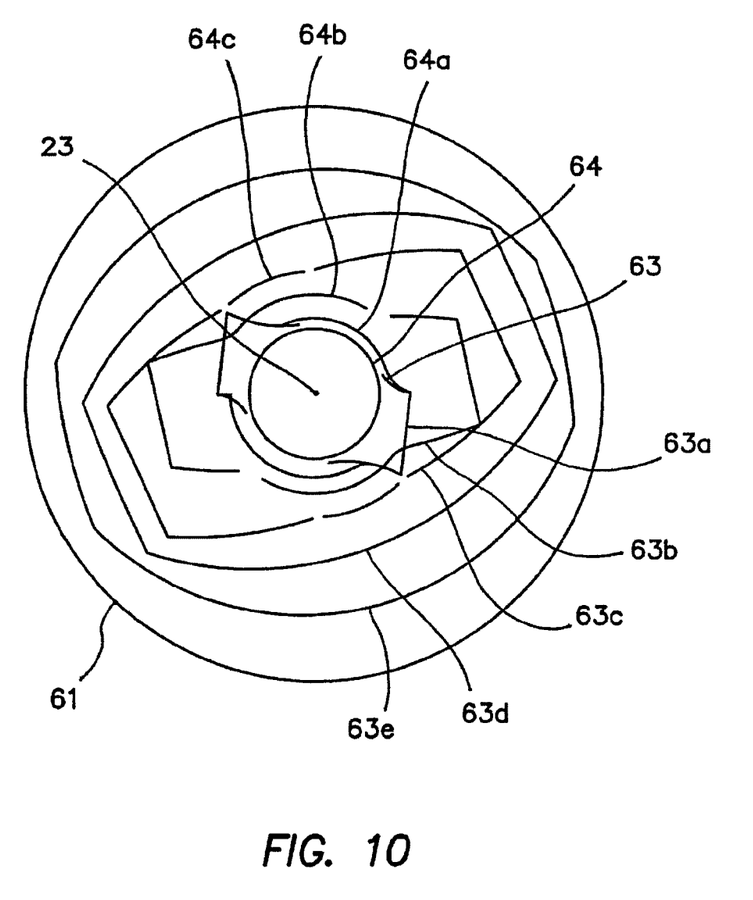
FIG. 10 is a schematic view illustrating each of the FIGS. 4-9 super-imposed to facilitate an understanding of the blunt cone tip and its twisted configuration according to the present invention.

In the progressive views of FIGS. 5-7, the circle 64 is further designated with a lower case letter a, b or c, respectively; similarly, the rectangle 63 is further designated with a lower case letter a, b, c, d or e, respectively, in FIGS. 5-9. In FIG. 10, the circles 64, 64a-64c and the rectangles 63, 63a-63e are superimposed on the axis 23 to show their relative sizes, shapes and angular orientations.

A preferred method of operating the trocar system 10 benefits significantly from this preferred shape of the blunt cone tip 27. With a conical configuration at the distal point and a rectangular configuration at a distal portion of the tip, the tip 27 appears much like a flathead screwdriver having a cone at its tip. Specifically, the blunt tip includes a conical structure extending outward from the end surfaces 58 and 59 that serves to direct the obturator through the abdominal wall and peritoneum. The cone tip has a radius of approximately 0.025". The incorporation of the cone onto the rectangular configuration reduces the insertion force required to traverse the abdominal wall. An advantage of the obturator of the invention is it provides a safer and more controlled entry of the abdominal cavity.

It is preferable that the lengths of the end surfaces 58 and 59 are aligned parallel with the fibers of each muscle layer. With this shape, the blunt cone tip can be used to locate or pinpoint a desired location and penetrate the abdominal wall. A simple back and forth twisting motion of the blunt cone tip tends to separate the fibers along natural lines of separation, opening the muscle layer to accept the larger diameter of the cannula 12. By the time the first layer is substantially penetrated, the conical and twisted configuration of the blunt cone tip 27 directs and turns the rectangle 63 more into a parallel alignment with fibers in the next layer. Again, the blunt cone tip facilitates penetration, and the twisting or dithering motion facilitates an easy separation of the fibers requiring a significantly reduced penetration and insertion force along the arrow 34.

It should be further noted that the blunt cone tip 27 is bladeless and atraumatic to organs and bowel within the peritoneal or abdominal cavity. The blunt cone tip 27 also minimizes tenting of the peritoneum and allows for a safe entry. The device is typically used in conjunction with the cannula 12 to create an initial entryway into the peritoneal cavity. The obturator 18 is first inserted through the valve housing 16 and into the cannula 12. The entire trocar system 10 is then inserted through the abdominal wall and into the peritoneal cavity. Once the cannula 12 is properly placed, the obturator 18 can be removed.

The invention facilitates a unique method of penetrating and separating tissue and could apply to any object with a blunt cone tip and generally flat sides. When inserted into the peritoneum the blunt cone tip requires very little area to move safely between tissue and muscle fibers. The device can then be rotated in alternating clockwise and counter-clockwise directions while the downward penetration force is applied. When rotated in alternating directions, the tissue is moved apart and a larger opening is created for a profile of greater cross sectional area to follow. This process continues with safety as the device enters the peritoneal cavity and moves to its operative position.

When the cannula 12 is ultimately removed, the size of the opening left in the tissue is minimal. Importantly, this opening is left sealed due to a dilating effect caused by the mere separation of fibers. Since there are no blades or sharp edges to cut muscle fiber, the healing process is significantly shortened.

The obturator 18 can be constructed as a single component or divided into multiple components such as the shaft 21 and the blunt cone tip 27. If the obturator 18 is constructed as a single component, it may be constructed of either disposable or reusable materials. If the obturator 18 is constructed as two or more components, each component can be made either disposable or reusable as desired for a particular configuration. In a preferred embodiment, the obturator is constructed as a single component made from a reusable material such as metal (e.g., stainless steel) or an autoclavable polymer to facilitate re-sterilization.

In another embodiment of the invention, the blunt cone tip 27 can be coated or otherwise constructed from a soft elastomeric material. In such a case, the material could be a solid elastomer or composite elastomer/polymer.

The shaft 21 of the obturator 18 could be partially or fully flexible. With this configuration, the obturator 18 could be inserted through a passageway containing one or more curves of virtually any shape. A partially or fully flexed obturator 18 could then be used with a flexible cannula 12 allowing greater access to an associated body cavity.

The obturator 18 could also be used as an insufflation needle and provided with a passageway and valve to administer carbon dioxide or other insufflation gas to the peritoneal cavity. The obturator 18 could also be used with an insufflation needle cannula, in which case removal of the obturator 18 upon entry would allow for rapid insufflation of the peritoneal cavity.

It will be understood that many modifications can be made to the disclosed embodiments without departing from the spirit and scope of the invention. For example, various sizes of the surgical device are contemplated as well as various types of constructions and materials. It will also be apparent that many modifications can be made to the configuration of parts as well as their interaction. For these reasons, the above description should not be construed as limiting the invention, but should be interpreted as merely exemplary of preferred embodiments.

We claim:

1. A surgical obturator, comprising:
    an elongate shaft extending along a longitudinal axis between a proximal end and a distal end; and
    a bladeless tip disposed at the distal end of the shaft having a conical surface forming proximally into an outer surface and distally to a blunt surface, said outer surface extending distally to the conical surface and having a pair of opposing surfaces separated by a pair of side surfaces;
    wherein the conical surface extends proximally from the blunt surface and is formed into the pair of opposing surfaces such that a portion of the conical surface formed in the opposing surfaces defines an intersection that is generally U-shaped;
    wherein the side surfaces define short sides of a rectangle and the opposing surfaces define long sides of the rectangle in a cross-section taken perpendicular to the longitudinal axis and along the outer surface; and
    wherein the side surfaces increase in length with consecutive proximal cross-sections taken perpendicular to the longitudinal axis.

2. The surgical obturator of claim 1 wherein a cross-section taken perpendicular to the longitudinal axis and along the conical surface in the location where the conical surface is formed into the pair of opposing surfaces is defined by the opposing surfaces, side surfaces and the conical surface; wherein the conical surface in the cross-section appears as two oppositely disposed curves extending outwardly from the opposing surfaces.

3. The surgical obturator of claim 1 further including two end surfaces extending radially outwardly from the conical surface; wherein the conical surface extends distally of the end surfaces and the portion of the conical surface formed in the opposing surfaces extends proximally of the end surfaces.

4. The surgical obturator of claim 1 wherein the side surfaces are twisted about the axis.

5. The surgical obturator of claim 1 wherein the opposing surfaces transition from a generally flat configuration to a generally rounded configuration with consecutive proximal cross-sections perpendicular to the longitudinal axis.

6. The surgical obturator of claim 1 wherein a plane drawn through the longitudinal axis defines two symmetrical halves in a cross-section of the tip taken perpendicular to the longitudinal axis.

7. The surgical obturator of claim 1 wherein a cross-section of the conical surface defines a circle having a circular area that increases with consecutive proximal cross-sections.

8. The surgical obturator of claim 1 wherein the obturator is configured as an insufflation needle and provided with a passageway to administer insufflation gas.

9. The surgical obturator of claim 1 wherein the side surfaces extend radially outwardly with progressively proximal positions along the longitudinal axis.

10. The surgical obturator of claim 1 wherein the tip twists radially from a distal end of the tip to a proximal end of the tip.

11. A surgical obturator, comprising:
an elongate shaft extending along a longitudinal axis between a proximal end and a distal end; and
a bladeless tip disposed at the distal end of the shaft having a conical surface forming proximally into an outer surface and distally to a blunt surface, said outer surface extending distally to the conical surface and having a pair of opposing surfaces separated by a pair of side surfaces;
wherein the conical surface extends proximally from the blunt surface and is formed into the pair of opposing surfaces such that a portion of the conical surface formed in the opposing surfaces defines an intersection that is generally U-shaped;
wherein the side surfaces are twisted about the axis in a first radial direction and a second radial direction opposite to the first radial direction.

12. The surgical obturator of claim 11 wherein the side surfaces define short sides of a rectangle and the opposing surfaces define long sides of the rectangle in a cross-section taken perpendicular to the longitudinal axis and along the outer surface.

13. The surgical obturator of claim 11 wherein the side surfaces increase in length and then decrease in length with consecutive proximal cross-sections perpendicular to the longitudinal axis.

14. A surgical obturator, comprising:
an elongate shaft extending along a longitudinal axis between a proximal end and a distal end; and
a bladeless tip disposed at the distal end of the shaft having a conical surface forming proximally into an outer surface and distally to a blunt surface, said outer surface extending distally to the conical surface and having a pair of opposing surfaces separated by a pair of side surfaces;
wherein the conical surface extends proximally from the blunt surface and is formed into the pair of opposing surfaces such that a portion of the conical surface formed in the opposing surfaces defines an intersection that is generally U-shaped;
wherein a ratio of the lengths of the opposing surfaces to side surfaces decreases with progressively proximal cross-sections taken perpendicular to the longitudinal axis.

15. A surgical obturator, comprising:
an elongate shaft extending along a longitudinal axis between a proximal end and a distal end; and
a bladeless tip disposed at the distal end of the shaft having a conical surface forming proximally into an outer surface and distally to a blunt surface, said outer surface extending distally to the conical surface and having a pair of opposing surfaces separated by a pair of side surfaces;
wherein the conical surface extends proximally from the blunt surface and is formed into the pair of opposing surfaces such that a portion of the conical surface formed in the opposing surfaces defines an intersection that is generally U-shaped;
wherein a ratio of the lengths of the opposing surfaces to the side surfaces decreases and then increases with progressively proximal cross-sections taken perpendicular to the longitudinal axis.

\* \* \* \* \*